US009930883B2

(12) United States Patent
Elliott et al.

(10) Patent No.: US 9,930,883 B2
(45) Date of Patent: Apr. 3, 2018

(54) COMPOSITIONS AND METHODS FOR PRESERVATION OF MATERIALS IN THE AMORPHOUS STATE

(71) Applicant: University of North Carolina Charlotte, Charlotte, NC (US)

(72) Inventors: Gloria Elliott, Harrisburg, NC (US); Babak Bagheri, Shorewood, WI (US)

(73) Assignee: UNIVERSITY OF NORTH CAROLLINA CHARLOTTE, Charlotte, NC (US)

( * ) Notice: Subject to any disclaimer, the term of this patent is extended or adjusted under 35 U.S.C. 154(b) by 0 days.

(21) Appl. No.: 14/969,624

(22) Filed: Dec. 15, 2015

(65) Prior Publication Data
US 2016/0165879 A1 Jun. 16, 2016

Related U.S. Application Data

(60) Provisional application No. 62/091,724, filed on Dec. 15, 2014.

(51) Int. Cl.
| | |
|---|---|
| *C12N 5/04* | (2006.01) |
| *A01N 1/00* | (2006.01) |
| *A01N 1/02* | (2006.01) |
| *C12N 1/04* | (2006.01) |
| *A23L 3/3553* | (2006.01) |
| *A23L 3/3562* | (2006.01) |

(52) U.S. Cl.
CPC .......... *A01N 1/0231* (2013.01); *A23L 3/3553* (2013.01); *A23L 3/3562* (2013.01); *C12N 1/04* (2013.01); *A23V 2002/00* (2013.01)

(58) Field of Classification Search
CPC ...... A01N 1/0231; A01N 1/0221; A01N 1/00; C12N 1/04
See application file for complete search history.

(56) References Cited

U.S. PATENT DOCUMENTS 7,883,664 B2    2/2011   Yoo
2013/0089912 A1    4/2013   Elliott

OTHER PUBLICATIONS

Bagheri, B., Dynamic water sorption in trehalose-salt mixtures: Effect of composition on retention of the amorphous state. The University of North Carolina at Charlotte, ProQuest Dissertations Publishing (2014) 68 pages, 1585330.*
Maria F. Mazzobre, Gonzalo Soto, Jose' M. Aguilera, Mari'a P. Buera. 2000. "Crystallization kinetics of lactose in sytems co-lyofilized with Trehalose, analysis by differential scanning calorimetry". Food Research 34: 903-911.
Alexandra Simperler, Andreas Kornherr, Reenu Chopra, P. Arnaud Bonnet, William Jones, W. D. Samuel Motherwell, and Gerhard Zifferer. 2006. "Glass Transition Temperature of Glucose, Sucrose, and Trehalose: An Experimental and in Silico Study". Phys. Chem. 110: 19678-19684.

(Continued)

*Primary Examiner* — Kara Johnson
(74) *Attorney, Agent, or Firm* — Thomas Horstemeyer, LLP (57) ABSTRACT

The present disclosure provides methods and compositions including a sugar and a choline hydrogen phosphate salt for preservation and stabilization of materials in the amorphous state. The compositions and methods suppress the formation of crystals in materials in the amorphous state.

22 Claims, 5 Drawing Sheets

(56) References Cited

OTHER PUBLICATIONS

Danforth P. Miller, Rebeccah E Anderson, Juan J. de Pablo. 1998. "Stabilization of lactate dehydrogenase following freeze-thawing and vacuum drying in the presence of trehalose and borate". Pharmaceutical Research 15, No. 8:1215-1221.

Ye Sun, Lei Zhu, Tian Wu, Ting Cai, Erica M. Gunn, Lian Yu. 2012. "Stability of Amorphous Pharmaceutical Solids: Crystal Growth Mechanisms and Effect of Polymer Additives". AAPS 14, No. 3: 380-388.

Alex Patist, Hans Zoerb. 2005. "Preservation mechanisms of Trehalose in food and biosystems". Colloids and Surfaces B: Biointerfaces 40: 107-113.

Nicole E. Hunter, Duncan Q. M. Craig, Peter S. Belton, Christopher S. Frampton. 2010. "The use of dynamic vapour sorption methods for the characterization of water uptake in amorphous trehalose". Carbohydrate Research 345: 1938-1944.

G.K. van der Wela, O.C.G. Adan. 1999. "Moisture in organic coatings—a review". Organic Coatings 37: 1-14.

Hector A. Iglesias, Jorge Chirife and Mar a P Buera. 1997."Adsorption isotherm of amorphous trehalose". Sci Food Agric 75: 183-186.

Song Maio, Yrjo H. Roos. 2006."Crystallization Kinetics and X-ray Diffraction of Crystals Formed in Amorphous Lactose". Food Science 70, No. 5:350-358.

M. F. Mazzobre,M. P. Longinotti,H. R. Corti, M. P. Buera. 2001. "Effect of Salts on the Properties of Aqueous Sugar Systems, in Relation to Biomaterial Stabilization". Cryobiology 43: 199-210.

Satoshi Ohtake, Carolina Schebor, Sean P. Palecek, Juan J. de Pablo. 2004."Effect of pH, Counter ion, and phosphate concentration on the glass transition temperature of freeze-dried sugar-phosphate mixtures". Pharmaceutical Research 21, No. 9:1615-1621.

Ranjan Sitaula, Sankha Bhowmick. 2006. "Moisture sorption characteristics and thermophysical properties of trehalose-PBS mixtures". Cryobiology 52: 369-385.

D.P. Miller, J.J. de Pablo, H.R. Corti. 1997."Thermophysical properties of trehalose and its concentrated aqueous solutions". Pharmaceutical Research 14, No. 7: 578-590.

Danforth P. Miller, Juan J. de Pablo, Horacio R. Corti. 1999. "Viscosity and Glass Transition Temperature of Aqueous Mixtures of Trehalose with Borax and Sodium Chloride". Phys. Chem. B 103: 10243-10249.

James J. Stachecki, Jacques Cohen and Steen Willadsen. 1998. "Detrimental Effects of Sodium during Mouse Oocyte Cryopreservation". Biology of Reproduction 59: 395-400.

Katherine D. Weaver, Regina M. Vrikkis, Matthew P. Van Vorst, Jonathan Trullinger, Ranganathan Vijayaraghavan, David M. Foureau, Iain H. McKillop, Douglas R. MacFarlane, Joanna K. Kruegerb and Gloria D. Elliott. 2012. "Structure and function of proteins in hydrated choline dihydrogen phosphate ionic liquid". Phys. Chem. 14: 790-801.

A.M. Elmonsef Omar, Yrjo H. Roos. 2007."Glass transition and crystallization behaviour of freeze-dried lactose-salt mixtures". LWT—Food Science 40: 536-543.

D.J. Burnett, F. Thielmann, T. Sokoloski, J. Brum. 2006. "Investigating the moisture-induced crystallization kinetics of spray-dried lactose". Pharmaceutics 313: 23-28.

Carolina Schebor, Maria Florencia Mazzobrea, María del Pilar Bueraa. 2010. "Glass transition and time-dependent crystallization behavior of dehydration bioprotectant sugars". Carbohydrate Research 345: 303-308.

Richard W. Hartel, Roja Ergun, and Sarah Vogel. 2011. "Phase/State Transitions of Confectionery Sweeteners: Thermodynamic and Kinetic Aspects". Comprehensive Reviews in Food Science and Food Safety, vol. 10: 17-32.

Sun Y, Xi H, Chen S, Ediger MD, Yu L. 2008. "Crystallization near glass transition: transition from diffusion-controlled to diffusionless crystal growth studied with seven polymorphs". Phys. Chem. B 112: 5594-5601.

Weng L & Elliott G. 2015. Distinctly Different Glass Transition Behaviors of Trehalose Mixed with Na2HPO4 or NaH2PO4: Evidence for its Molecular Origin. Pharmaceutical Research, Jul. 2015, vol. 32: 7, pp. 2217-2228.

Weng et al (Elliott). Application of the Kwei equation to model the Tg behavior of binary blends of sugars and salts. Feb. 2014 Cryobiology, vol. 68, Issue 1, pp. 155-158.

\* cited by examiner

COMPOSITIONS AND METHODS FOR PRESERVATION OF MATERIALS IN THE AMORPHOUS STATE

CROSS-REFERENCE TO RELATED APPLICATIONS

This application claims priority to U.S. provisional applications entitled, "Choline Hydrogen Phosphate as a Sugar Crystallization Suppression Agent," having Ser. No. 62/091,724, filed on Dec. 15, 2014, which is entirely incorporated herein by reference.

STATEMENT REGARDING FEDERALLY SPONSORED RESEARCH OR DEVELOPMENT

This invention was made with Government support under GM101796 awarded by the National Institutes of Health. The Government has certain rights in this invention.

BACKGROUND

In the pharmaceutical and food industries, the amorphous state of sugars is produced intentionally as an inactive excipient to stabilize active materials that have low stability in aqueous media. The amorphous state has enhanced thermodynamic properties compared to the crystalline phase. Due to the high viscosity and low molecular mobility in the amorphous glass or meta-stable liquid state (compared to crystals), preservation of bio-materials, such as protein or membrane components, is possible. Thus, extended shelf life of biologics can be achieved in the matrices of sugar glasses.

Many current biological therapeutics and bio-based medicines result in high costs for production, storage, and transport since many are stored and transported at cryogenic temperatures. Due to these costs, alternatives to cryopreservation are being sought, such as preservation of biological materials in a dry state, achieved by removing water and/or cooling the formulation to an extent to create an amorphous solid (e.g., glassy state solid) and/or meta-stable liquid. In this state degradation reactions are prevented and the extreme cryogenic temperatures for storage and transport are not needed.

However, the glassy state is thermodynamically meta-stable and tends to convert to a crystal eventually, with a rate dependent on the temperature and moisture content, which will deteriorate the quality of pharmaceuticals and food and decrease the viability of biologics. Thus, stabilization of the glassy amorphous form and other amorphous forms is desirable to preserve biomaterials and food products during storage for extended times. Some sugars have been used for preservation of biological material in a glassy state (e.g., trehalose, sorbitol, mannitol, which can form glasses at ambient conditions); however, deviations from ideal temperatures and humidities can cause samples to come out of the glassy state, which can cause problems with stability.

SUMMARY

Briefly described, embodiments of the present disclosure provide methods and compositions for preservation of materials in the amorphous state.

Embodiments of methods for preservation of a biomaterial according to the present disclosure include combining the biomaterial with a preservative composition comprising a sugar or sugar alcohol and a salt comprising choline hydrogen phosphate ($HPO_4^{-2}$), and converting the material the amorphous state.

Embodiments of the present disclosure of methods of suppressing crystallization of a composition in an amorphous state comprising a sugar or sugar alcohol include combining the sugar or sugar alcohol with a salt comprising choline hydrogen phosphate ($HPO_4^{-2}$) in an amount effective to increase the amount of time to formation of crystals in the composition when in the amorphous state as compared to a composition in the amorphous state made without the choline hydrogen phosphate.

Embodiments of preservative compositions of the present disclosure include a sugar or sugar alcohol and a salt comprising choline hydrogen phosphate ($HPO_4^{-2}$), the composition having a salt:sugar ratio effective to suppress the formation of crystals in the composition in the amorphous state. In embodiments of such preservative compositions, the salt:sugar ratio is effective to suppress crystal formation in the composition such that the amount of time to formation of crystals in the presence of moisture is increased over the amount of time to crystal formation in a comparative composition that is the same as the preservative composition except for having a greater amount of choline dihydrogen phosphate than the salt of the preservative composition.

The present disclosure provides embodiments of compositions including a living biomaterial and a preservative composition, the preservative composition comprising a sugar or sugar alcohol and a salt comprising choline hydrogen phosphate ($HPO_4^{-2}$). In embodiments the material is in an amorphous state and the amount of time to formation of crystals in the material in the presence of moisture is increased over the amount of time to crystal formation in a composition comprising the biomaterial without the preservative composition.

Other methods, compositions, plants, features, and advantages of the present disclosure will be or become apparent to one with skill in the art upon examination of the following drawings and detailed description. It is intended that all such additional compositions, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings.

DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Any publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biochemistry, organic chemistry, molecular biology, biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a cell" includes a plurality of cells. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing the disclosed subject matter, the following terminology will be used in accordance with the definitions set forth below.

As used herein, the terms "amorphous state," refers to a non-crystalline state of matter, including amorphous liquids and solids, such as a non-crystalline solid and/or meta-stable liquid. Amorphous liquids and amorphous solids are collectively referred to herein as "amorphous materials." An amorphous solid is a solid with a non-crystalline structure which can include hard glasses as well as non-crystalline, near-glass rubbery amorphous solids, where the material is not a complete glass but does not exhibit crystal formation (e.g., still retains the amorphous status). The terms "amorphous solid," "amorphous glass," and "glassy state" may be used herein to refer generally to all forms of amorphous solids, including the hard glass sate as well as non-crystalline amorphous, near-glass, rubbery state.

Liquids in the amorphous state are referred to herein as "amorphous liquids," "meta-stable liquids" and/or "super-cooled liquids" (e.g., liquids below the freezing point that have not solidified/crystallized). Glasses exhibit a glass transition from an amorphous liquid or fluid-like rubbery state to a solid glassy state at the glass transition temperature ($T_g$). In embodiments, amorphous glass can be formed by cooling and/or dehydrating a viscous liquid into the glass state by various methods, a process also known as "vitrification." When a material in the glassy state reaches a temperature above the Tg, the matter can begin to form crystals. Typically, adding moisture in the form of water lowers the Tg of a material.

The term "biomaterial" as used in the present disclosure refers to living and/or naturally derived biological materials or cells (e.g., tissues, cells, or other biomolecules derived from a living organism) as well as biocompatible synthetic materials (e.g., man-made and/or engineered materials that can be used in conjunction with and without harm to living biomaterials (e.g., synthetic scaffolds for use with living cells).

As used herein, the term "biomolecule" refers to biological compounds such as, but not limited to: deoxyribonucleic acid (DNA), ribonucleic acid (RNA), nucleotides, oligonucleotides, nucleosides, proteins, peptides, polypeptides, selenoproteins, antibodies, protein complexes, peptide nucleic acids, combinations thereof, and the like. In particular, the biomolecule can include, but is not limited to, naturally occurring substances such as polypeptides, polynucleotides, glycoproteins, macromolecular polypeptide complexes, vitamins, co-factors, whole cells, eukaryotic cells, prokaryotic cells, microorganisms (such as, but not limited to, eubacteria, protozoa, archaea, fungi, algae, spores, apicomplexan, trematodes, nematodes, and mycoplasma), viruses (including, but not limited to, enveloped and nonenveloped viruses, DNA and RNA viruses, bacteriophages, retroviruses, etc.), nutraceutical compounds, or combinations thereof.

The phrase "bioactive agent" includes a biomolecule or other biocompatible compound that has some activity, use, and/or effect in a biological system or in relation to another biomolecule.

The terms "polypeptide" and "protein" as used herein refer to a polymer of amino acids of three or more amino acids in a serial array, linked through peptide bonds. The term "polypeptide" includes proteins, protein fragments, protein analogues, oligopeptides, and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The term "gene" or "genes" as used herein refers to nucleic acid sequences (including both RNA and/or DNA) that encode genetic information for the synthesis of a whole RNA, a whole protein, or any portion of such whole RNA or whole protein. A "gene" typically refers to a hereditary unit corresponding to a sequence of DNA that occupies a specific location on a chromosome and that contains the genetic instruction for a characteristic(s) or trait(s) in an organism. The term "gene product" refers to RNAs or proteins that are encoded by the gene.

As used herein, "isolated" means removed or separated from the native environment. An isolated compound or material (e.g., a cell, tissue, protein, etc.) indicates the compound or material is separated from its natural environment. Isolated compounds or materials are not necessarily purified.

The term "tissue" generally refers to a grouping of cells organized to cooperatively carry out a biological function and/or serve a biological purpose, such as forming all or part of an organ in an organism (e.g., connective tissue, endothelial tissue). While a "tissue" generally includes a grouping of similar cells, or cells of all the same type, a tissue may also include cells of more than one type where the group of cells as a whole serve a common purpose.

"Cells" as used herein, includes both prokaryotic and eukaryotic cells, and both plant cells (including monocots and dicots) and animal cells (e.g., avian, amphibian, reptile, and mammalian cells). In some embodiments mammalian cells (including but not limited to human, monkey, ape, dog, cat, mouse, rat, horse, goat, sheep, etc.) are preferred. Cells may reside in vitro or in vivo in a tissue in organ (though the tissue or organ is generally in vitro rather than in vivo in a host or subject).

As used herein the term "biocompatible" refers to the ability to co-exist with a living biological substance and/or biological system (e.g., a cell, cellular components, living tissue, organ, etc.) without exerting undue stress, toxicity, or adverse effects on the biological substance or system.

As used herein the term "suppress" or "substantially suppress" with respect to crystal formation means to slow or reduce the formation of crystals in a material under conditions that would induce crystal formation in a control material (e.g., without a preservative composition of the present disclosure). This does not indicate that crystal formation is completely inhibited under all conditions but that crystal formation is reduced or less likely to occur; the material resists crystallization.

DISCUSSION

The embodiments of the present disclosure encompass methods and compositions for preservation of materials in the amorphous state and suppressing crystallization in materials in the amorphous state, including the amorphous glass state or near glassy region as well as meta-stable amorphous liquids. Compositions of the present disclosure include a preservative composition including a sugar or sugar alcohol and a salt, where the salt includes choline as the cation and hydrogen phosphate ($HPO_4^{-2}$) as the anion. Methods of the present disclosure include preservation of materials, including but not limited to biomaterials, using the choline hydrogen phosphate (CHP) preservative compositions of the present disclosure.

Sugars have been evaluated for stabilizing and preserving materials in the glassy state. The stabilizing mechanism of sugars is mainly two-fold. Kinetically, the deteriorative reactions can be inhibited in sugar glasses due to their very high viscosity and low molecular mobility. Sugars such as trehalose were also found to associate with and stabilize proteins and lipid membranes according to the "water replacement" hypothesis. However, though such sugar compositions perform well if stored in appropriate humidity and temperature conditions, they can become thermodynamically unstable during long-term storage of food and living biomaterials if shipping or storage conditions deviate from ideal or packages are compromised, because the glassy state is meta-stable and will drive towards the more stable crystalline state. Once this crystal state forms, it cannot be returned to the glassy state.

For example, water exhibits a plasticizing effect on sugar glasses by the depression of the glass transition temperature ($T_g$). The $T_g$ value of binary mixture of sugars-water (i.e. trehalose, sucrose) decreases with an increase of the moisture content, following a non-linear function as described by the Gordon-Taylor equation, $$T_g = \frac{c_s T_{g,s} + kc_w T_{g,w}}{c_s + kc_w} \quad (1.1)$$

where $c_s$ and $c_w$ are the mass fractions of the sugar and of water, $T_{g,s}$ and $T_{g,w}$ are their $T_g$ values, respectively, and k is a constant.

When the $T_g$ is depressed below the storage temperature, this can promote the sugar crystallization process, resulting in a decrease in viscosity and the collapse of the solid structure.

Amorphous sugar-liposome compositions have been prepared and stored at 40° C. in the 58% RH environment. It was found that the absorbed water in trehalose contributed to the formation of trehalose dihydrate in the matrix, and the moisture content of trehalose dihydrate remained constant (9.54%) in the RH environment of up to 92%.

A number of efforts have been made to retain the amorphous state of sugars and suppress crystallization by formulating them with suitable additives. For example, the moisture absorption isotherm of amorphous trehalose and trehalose/maltodextrin (50% dry basis) systems at 25° C. has been determined. It was found that the isotherm of pure trehalose exhibited a plateau at 44% RH and above, which indicated the formation of trehalose dihydrate crystals. However, the crystallization of trehalose was retarded in the presence of maltodextrin, except for humidification at 75% RH. Similarly, the addition of maltodextrin was also observed to delay the crystallization of lactose. In addition, the crystallization of sucrose and trehalose was reduced by the addition of polymeric compounds such as poly(vinyl pyrrolidone) (PVP), even though co-lyophilized sugar-PVP mixtures took up essentially the same amount of water as predicted by the weight average of individual isotherms. Since the isothermal absorption at $T>T_g$ can expedite the crystallization, the addition of high molecular weight compounds to sugars can help increase the glass transition temperature above the storage or experiment temperature, resulting in the delay of the sugar crystallization. Molecular interactions between sugar and polymer also play a role in the inhibition of crystal formation.

However, it was also discovered that the addition of some salts could affect the characteristics of moisture sorption and sugar crystallization without changing the $T_g$ of the compositions significantly. For instance, it was reported that the crystallization of trehalose dihydrate at 44% RH and 25° C. was inhibited upon the addition of magnesium chloride (molar ratio of trehalose to $MgCl_2$ was 5:1). The degree of crystallization determined by differential scanning calorimetry (DSC) was found to be only 50% while the water vapor uptake was higher than other compositions under investigation (e.g., trehalose with NaCl, KCl or $CaCl_2$), which was suggested to be attributed to the high charge/size ratio of $Mg^{2+}$. However, not all salts are effective to suppress crystallization. For instance, given that phosphate-buffered saline (PBS) is the most commonly used in vitro medium for cell culture, the moisture desorption characteristics of aqueous trehalose/PBS systems was studied. The presence of PBS promoted the formation of trehalose dihydrate crystals instead of inhibiting it and shifted the desorption isotherm from type II to type III (characterized by the Brunauer-Emmett-Teller equation), which could be detrimental for the stabilization of liable biologics. It was observed that at 37.5% RH the pure trehalose and trehalose/PBS mixture with a molar ratio of 20:1 did not show any crystals but the system with the molar ratio of 10:1 and lower showed clear crystalline peaks on the DSC thermograms.

Choline dihydrogen phosphate (CDHP) has been evaluated as a stabilizing agent for proteins and DNA. The $T_g$ of anhydrous trehalose/choline dihydrogen phosphate mixtures varied in a non-monotonic manner with the mass fraction of trehalose. Interestingly, it was observed that freeze-dried sugar/phosphate mixtures had different glass transition behaviors when the pH values of their pre-lyophilized aqueous solutions were adjusted. For example, the addition of phosphate ions to trehalose could increase the $T_g$ only at pH values greater than 6.6. At lower pH values the $T_g$ was decreased upon the addition of phosphate. Although the salts composed of choline or sodium and dihyrogen phosphate ($H_2PO_4^-$) are potentially useful additives for trehalose-based biomolecule preservation formulations, the effect of these cations and anions on the moisture absorption characteristics and the retention of glassy state have not been fully determined or clarified.

The example below describes a dynamic vapor sorption experiment that investigated the effects of different electrolyte additives (choline ($Ch^+$) or sodium ($Na^+$) as the cation, and hydrogen phosphate ($HPO_4^{2-}$) or dihydrogen phosphate ($H_2PO_4^-$) as the anion) on the moisture uptake kinetics and the stability of amorphous trehalose compositions. It was surprisingly found that choline outperformed sodium as the cation and hydrogen phosphate ($HPO_4^{-2}$) as the anion had a greater ability to suppress crystallization than the more common dihydrogen phosphate ($H_2PO_4^-$). Thus, the present disclosure provides compositions and methods for preserving materials and suppressing crystallization of materials in the amorphous state using a sugar/salt preservative composition with the salt choline hydrogen phosphate (CHP).

Preservative/Stabilizing Compositions:

Embodiments of the present disclosure include preservative compositions including a sugar or sugar alcohol and a salt that includes choline hydrogen phosphate CHP. In CHP the organic cation is the quaternary ammonium cation choline and the anion is the organic phosphate anion hydrogen phosphate ($HPO_4^{-2}$) (also sometimes referred to as monohydrogen phosphate to distinguish it from the dihydrogen phosphate). In embodiments the composition has a salt:sugar ratio effective to suppress the formation of crystals in the composition while in the amorphous glass state, metastable liquid, and near glassy amorphous region (e.g., the materials may partially or completely transition out of the glassy state but retain an amorphous, non-crystalline state due to the continued resistance to crystallization provided by the composition of the present disclosure).

In embodiments, the composition has a salt:sugar ratio effective to suppress crystal formation in the composition at temperatures and/or humidities that would typically result in crystallization. In embodiments, the compositions of the present disclosure have a salt:sugar ratio effective to suppress crystal formation at ambient temperature (e.g., room temperature, about 20-26° C.) and humidity (e.g., 20-70%). In some embodiments, the salt:sugar ratio can be effective to suppress crystal formation even when exposed to temperatures higher than room temperature or extreme temperatures, and humidity above 90% for periods of exposure. In embodiments, the composition resists the formation of crystals for a longer period of time than the amount of time to crystal formation in a comparative composition made with choline dihydrogen phosphate (CDHP) as the salt and/or with CDHP present in an amount greater than 40% of the salt.

In embodiments the sugar can be, but is not limited to, trehalose, sucrose, fructose, glucose, and the like, and combinations of these. Sugar alcohols can include, but are not limited to mannitol, sorbitol, erythritol, glycerol, xylitol, etc., and combinations of these. In embodiments the sugar is trehalose. Trehalose is a natural alpha-linked disaccharide formed by an α,α-1,1-glucoside bond between two α-glucose units. Trehalose is a naturally occurring non-reducing sugar which is widespread in nature with molecular formula $C_{12}H_{22}O_{11}$ and a molar mass of 342.31 g/mol (anhydrous). It is usually prepared and sold as trehalose dihydrate, and, compared to other sugars with a similar structure, trehalose is slightly more soluble in water at 80° C. and higher temperatures. Owing to its distinct molecular structure and physico-chemical properties, trehalose is a very stable disaccharide and has been used as a cryoprotectant for freeze-dried foods and for lyophilization of bacteria, and preservation of proteins and lipid membranes.

The salt in the compositions of the present disclosure is an organic salt made of an organic cation comprising choline and organic anion including CHP. In embodiments, the anion can also include some proportion of CDHP, but the compositions of the present disclosure have a sufficient amount of CHP to improve the suppression of crystal formation in the amorphous materials over that of compositions including CHP as the sole or a significant anion. In embodiments, the compositions of the present disclosure have improved suppression of crystal formation (e.g., longer time to crystal formation in the same conditions (e.g., temperature, humidity, etc.)) as compared to a comparative composition where the only difference is a greater amount of CDHP in the composition. In other words, the comparative composition has the same sugar and the same salt:sugar ratio, but the composition has a greater amount of CDHP than in the composition of the present disclosure.

In embodiments, the compositions of the present disclosure have about 40% or more CHP in the salt. In embodiments the CHP includes about 50% or more of the salt. In embodiments, the CHP includes about 40% to about 90% of the salt. In embodiments it is desirable to limit the amount of CDHP present in the salt. In embodiments, the salt comprises about 60% or less wt percent CDHP. In embodiments, the salt comprises about 50% or less CDHP.

The proportion of CHP can be manipulated to adjust the pH of the preservative composition of the present disclosure. For instance a choline phosphate salt including about 40-50% CHP produces a salt having a pH of about 7-7.4, the preferred pH of most biologics. Increasing the amount of CHP increases the pH of the salt, and thus the preservative composition. In embodiments, the preservative composition has a pH of about 7.0 or greater. In embodiments, the preservative composition has a pH between about 7.0 and 10.0. In embodiments, the preservative composition has a pH of about 7.4.

As mentioned above, the salt:sugar ratio of the compositions of the present disclosure affects the ability of the preservative composition to suppress crystal formation in the composition when in the amorphous state. The examples below demonstrate that in some simulated stress conditions (e.g., increased humidity) increasing the salt:sugar ratio increased the suppression of crystal formation. In some embodiments, the preservative composition of the present disclosure the salt:sugar ratio is about 0.25 or greater, about 0.50 or greater, as well as intervening ranges. In embodiments, the salt:sugar ratio is between about 0.2 and 2.0. As described in the examples below, the compositions of the present disclosure have demonstrated capability to suppress crystal formation in amorphous materials at salt:sugar ratios of about 0.2 and greater in environmental conditions involving high humidity for extended periods of time. In some embodiments, the preservative compositions of the present disclosure can provide protection against crystallization at lower salt:sugar ratios in situations where the conditions are less drastic (e.g., shorter exposures to high humidity, smaller temperature fluctuations, etc.) such as would likely be experienced during transport of amorphous state materials. Thus, in embodiments, the salt:sugar ratio of the present disclosure is about 0.1 or greater. In embodiments, the salt:sugar ratio of the present disclosure is about 0.1 to about 2.0.

The preservative compositions of the present disclosure can be used directly to stabilize sugars in the amorphous glassy or near-glassy state (e.g., in the food and health industries, such as candies, lozenges, etc.) or meta-stable liquid state. The sugar/salt preservative compositions can be combined with other ingredients and then converted to the amorphous state by methods known in the art to make amorphous sugar materials including the preservative compositions of the present disclosure.

The preservative compositions of the present disclosure can also be used for the preservation and stabilization of biomaterials in the amorphous glass state or the metastable liquid state (e.g., supercooled or supersaturated). Thus, in embodiments, the present disclosure also includes compositions including a biomaterial (e.g., living cells, tissues, peptides, nucleic acids, viruses, and other biomolecules, and the like as described above) combined with a preservative composition of the present disclosure, where the preservative composition within (e.g., mixed with, in/around) the material is in an amorphous glass state or the metastable liquid state. In embodiments, the preservative composition forms an amorphous state matrix material that forms within and/or around the biomaterial for stabilization/preservation of the biomaterial.

The presence of the preservative composition of the present disclosure in the material provides superior preservation for the biomaterial because the preservative compositions of the present disclosure resist crystallization, thus increasing the amount of time to formation of crystals in the preservative composition/matrix in the presence of moisture over the amount of time to crystal formation in a comparative composition without the preservative composition or with a different preservative composition. For instance, the preservative compositions of the present disclosure resist crystal formation in a preserved biomaterial for a greater amount of time than a preservative composition made with a choline dihydrogen phosphate (CDHP) salt or a comparative salt having a greater amount of CDHP. In embodiments, the pH of the material is about 7.0 or greater and the salt of the preservative composition comprises about 60% or less of CDHP. In embodiments, the pH of the material is about 7.0 or greater and the salt of the preservative composition comprises about 50% or less of CDHP.

In some embodiments of the present disclosure, the preservative composition has a glass transition temperature of above room temperature (e.g. 20-26° C. or greater) and retains the ability to resist crystallization even at temperatures above the $T_g$ and/or at elevated relative humidity. The preservative compositions of the present disclosure provide the ability to resist crystallization at a wide range of humidity and temperature swings, providing advantages in storage and transportation of materials in the amorphous state.

Although it appears that the resistance to crystal formation provided by the choline hydrogen phosphate may also be independent of any change in the $T_g$, since suppression of crystallization is seen even in the supersaturated liquid state (as demonstrated in the examples below), increased glass transition temperatures are also helpful to preserve the materials in the glassy state and resist crystal formation at typical storage and transport temperatures. The preservative compositions of the present disclosure can provide increased resistance to crystallization in both amorphous glassy state materials as well as amorphous liquids (e.g., supercooled/supersaturated metastable liquids), as well as in some embodiments increasing the $T_g$. For the food industry the ability to maintain amorphous state preserves shelf life. For biological materials, this feature helps to reduce the need to maintain cryogenic temperatures until the material is used, therefore reducing costs of storage and transportation of biomaterials until use.

Thus, due to the advantages provided by the preservative compositions of the present disclosure these compositions are also useful for methods of preserving biomaterials and methods of suppressing crystallization of amorphous state materials.

Methods:

The present disclosure also provides methods of preserving materials and biomaterials using the preservative compositions of the present disclosure and methods of suppressing crystallization of a composition in the amorphous state including a sugar or sugar alcohol.

In embodiments, methods of the present disclosure include combining a sugar or sugar alcohol with a salt including CHP and converting the mixture to an amorphous state (e.g., glass, metastable liquid, etc.), where the CHP is present in an amount effective to increase the amount of time to formation of crystals in the amorphous state compositions. In embodiments the time to crystal formation is increased (e.g., greater than) the amount of time to crystal formation in a comparative composition made without the choline hydrogen phosphate. In embodiments the time to crystal formation is increased (e.g., greater than) the amount of time to crystal formation in a comparative composition made without with CDHP as the salt, with CDHP present in a greater amount than CHP, and/or with CDHP present in a weight percent of 40% or more of the salt.

In embodiments, methods of the present disclosure for preservation of a biomaterial include combining the biomaterial with a preservative composition comprising a sugar or sugar alcohol and a salt comprising choline hydrogen phosphate ($HPO_4^{-2}$) and then converting the material to the amorphous (glass and/or metastable liquid) state. In embodiments the preservative composition used in methods preservation of the biomaterial is as described above. In embodiments, the sugar can be, but is not limited, to sucrose, glucose, fructose, and trehalose. In embodiments, the sugar is trehalose. In embodiments, the preservative composition has salt:sugar ratios and pH as described above.

In embodiments, the material containing the preservative composition of the present disclosure is converted to the amorphous state using processes such as, but not limited to, dehydrating the material, cooling the material to a temperature less than the glass transition temperature and/or freezing temperature of the composition, or combinations of these methods. In embodiments, the method of cooling can be, but is not limited to, freezing, freeze-drying, vitrification, supercooling, cryopreservation, and the like. In embodiments, the method of drying/dehydrating can be, but is not limited to, heat drying, microwave drying (including but not limited to the methods described in U.S. Pat. No. 7,883,664), lyophilization, use of a desiccant, air-flow drying, spin drying, spray drying, and the like. In embodiments, combinations of the above drying and/or cooling methods can be used to convert the material to the amorphous (e.g., glassy, near-glass, supercooled/supersaturated liquid) state.

After cooling and/or drying, the compositions may then be stored for a desired time (e.g., one or two months, to one or two years, or more). In embodiments, the amorphous preserved material is stored at a temperature less than the glass transition temperature of the composition. In embodiments, the material is stored at a humidity less than standard humidity. Storage may be in any suitable container or vessel in any suitable device, such as a freezer, refrigerator, liquid nitrogen, etc., or at room temperature, depending upon the particular composition. However, in embodiments, even if the material is exposed to higher than ideal temperatures or humidity (even up to 90-100% humidity) for periods of time, the material preserved according to the methods of the present disclosure will maintain amorphous state and resist crystallization.

Following any desired storage, biomaterials, such as tissues, stabilized cells, biological scaffolds, virus compositions, etc., as described above, may be warmed (e.g., to a temperature above the glass transition temperature of the material) and/or rehydrated to provide the biomaterials in viable form. The biomaterials may then be used for whatever intended purpose, including but not limited to subsequent in vitro culturing, growing, or propagation thereof, and/or (in the case of tissues, grafts, scaffolds, or organs for implantation or transplantation) in vivo implantation or transplantation into a subject in need thereof.

Additional details regarding the tests and methods of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%)

within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

This example describes the preparation, testing, and analysis of a series of phosphate salts as additives to trehalose compositions in order to understand their effectiveness at suppressing crystallization and retaining the desired amorphous form.

Four salts were studied, with choline ($Ch^+$) or sodium ($Na^+$) as the cation, and hydrogen phosphate ($HPO_4^{2-}$) or dihydrogen phosphate ($H_2PO_4^-$) as the anion. Microwave-assisted processing was used to reach the amorphous state in a series of trehalose/salt compositions. These samples were then evaluated for moisture uptake characteristics and visually examined for the onset of crystallization. The results demonstrate that the crystal suppression efficacy increased with increasing concentration of salt in the mixture, with the exception of compositions containing $NaH_2PO_4$ in which samples at all salt:trehalose molar ratios crystallized within the same time period as pure trehalose. Of the salts evaluated, choline hydrogen phosphate was found to be the most effective for suppressing crystallization.

Materials and Methods

A stock solution of 30.8 wt % trehalose (1.3 M), made in 1×TE buffer (1×Tris-EDTA buffer, pH 8.0, consisting of 10 mM Tris-HCl and 1 mM EDTA), was used to prepare solutions with varying amounts of phosphate salts (salt to trehalose molar ratio (R) is 1:4.8, 1:2 and 1:0.7). Compositions of salts with trehalose in buffer solution were made by adding aliquots of the trehalose stock solution together with the appropriate mass of salt in order to achieve the desired molar ratios of salt to trehalose in a final volume of 1×TE buffer.

Choline hydrogen phosphate was prepared by increasing the pH of choline dihydrogen phosphate solution with choline hydroxide and then lyophilizing the composition to recover choline hydrogen phosphate. The salt was then added to an appropriate aliquot of 30.8 wt % trehalose stock solution to make the desired mixtures of trehalose/choline hydrogen phosphate.

In a custom-made 11% RH environmental chamber, a 100 µL droplet of the solution studied was pipetted on the treated side of Thermanox coverslips (Nunc, Thermo Fisher Scientific, Rochester, N.Y., Dia. 22 mm,) which was then placed on a custom turntable for microwave (SAM 255, CEM Corp., Matthews, N.C.) drying at 11% RH and 23.5±1.5° C. The end moisture content was measured below 0.105 $gH_2O/$gdw which is known to produce a glass transition temperature higher than room temperature in the case of aqueous trehalose solutions. The microwave-dried samples were transferred in the 11% RH environment into a fixed relative humidity jar of 61% RH since the previous study has found that amorphous trehalose was able to crystallize in environments with 44% RH and higher.

Specifically, in order to investigate moisture sorption in different trehalose/salt compositions at the 61% relative humidity, a closed environment with a stable relative humidity over the test duration was prepared. Supersaturated salt solutions of sodium bromide (prepared by following ASTM Protocol E 104-02) are capable of producing an environment with constant relative humidity of 61%. Kilner glass jars with rubber seals and clamps or Mason glass jars with screw caps are used as controlled humidity vessels (1 L, total height 159 mm, mouth Dia.89 mm). The dynamic vapor sorption (DVS) method was used to monitor moisture sorption in the microwave-processed trehalose samples before and after crystallization (crystals were detected visually in samples). The moisture uptake in trehalose/salt samples were monitored to evaluate the effect of salts on end moisture content at time zero after microwave processing at 11% RH. Moisture sorption trends in samples over the experiment duration while held in the preservation jars (61% RH) were also evaluated.

In this study, the gravimetric method was used to determine the dry weight of samples with different compositions (expressed in terms of mass of water per mass of solids). Briefly, Small volumes of solution were pipetted onto a glass fiber absorbent pad (CEM Corp., Matthews, N.C.) and then baked in a convection oven (VWR International, West Chester, Pa.) with silica gel desiccant for 48 hours at 95° C. (below the crystallization temperature of Trehalose). The sample was then cooled in a desiccator containing phosphorus pentoxide ($P_2O_5$) which maintained the humidity near 0% RH. By recording the initial wet mass and the bake-out dry mass, the dry weight of each composition was obtained.

Results and Discussion

Choline Dihydrogen Phosphate

Figure 1:
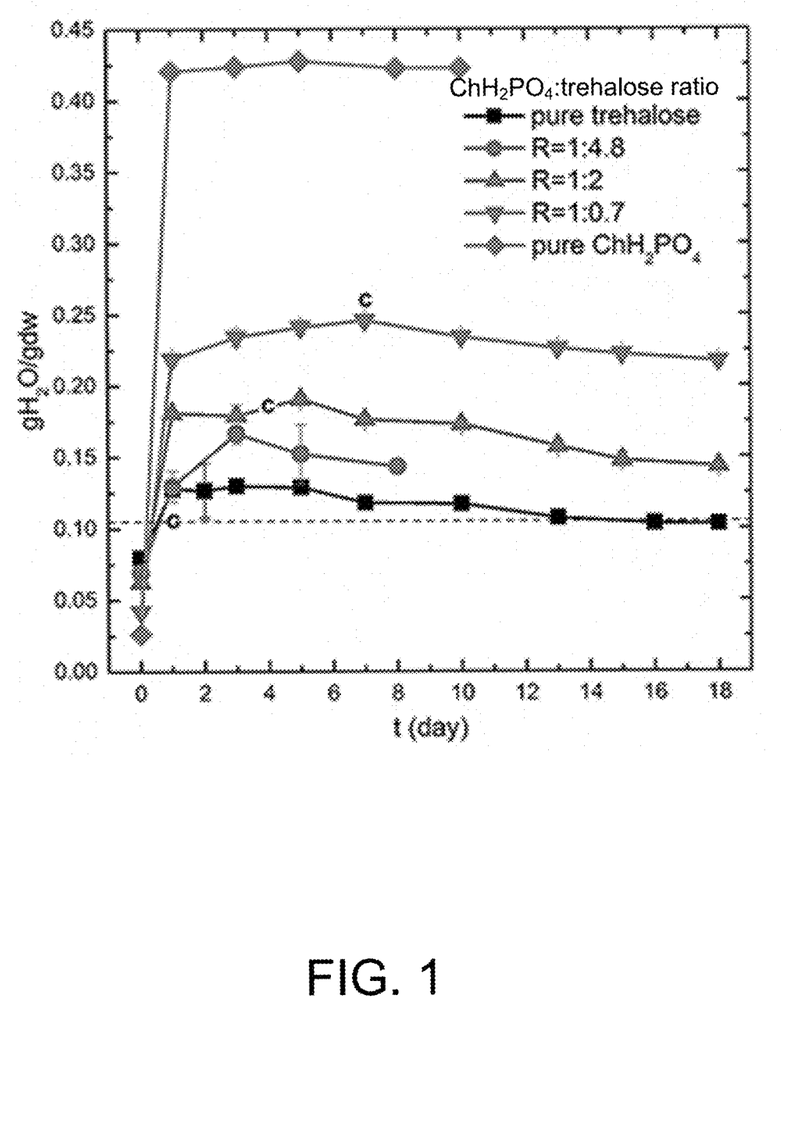
FIG. 1 is a graph illustrating moisture absorption kinetics in amorphous trehalose/$ChH_2PO_4$ systems of different ratios of $ChH_2PO_4$ to trehalose. The onset of crystallization as observed visually is indicated with the letter c.

FIG. 1 shows the moisture absorption kinetics in amorphous trehalose with or without the addition of choline dihydrogen phosphate. The absorption profile of pure trehalose indicates that the amorphous sample took up water until enough (~0.105 $gH_2O/g$ trehalose) was absorbed to enable the formation of trehalose dihydrate, which is consistent with previous findings. For pure trehalose samples, the formation of trehalose dihydrate crystals was observed at day 1. Upon the crystallization, the moisture content in the sample gently decreased to a $gH_2O/$gdw level of around 0.105 during the following 18 days.

When choline dihydrogen phosphate was added to trehalose, the onset of sugar crystallization was delayed. And the delay of trehalose crystallization was extended with the addition of more choline dihydrogen phosphate. One can also observe that the moisture uptake in the amorphous samples increased as more choline dihydrogen phosphate was added, even though the end moisture content right after the microwave-assisted drying is the highest in pure trehalose. Note that pure choline dihydrogen phosphate was found to be very hygroscopic with the most moisture uptake, and no crystallization of $ChH_2PO_4$ was observed. After the crystallization in the trehalose/$ChH_2PO_4$ systems, the moisture content likely fell back to a level still higher than 0.105 $gH_2O/$gdw, due to the hygroscopic nature of choline dihydrogen phosphate.

The maximum suppression of crystallization was observed in trehalose/$ChH_2PO_4$ systems with the highest molar ratio of $ChH_2PO_4$ to trehalose. Interestingly, given that trehalose/$ChH_2PO_4$ samples retained more moisture in 61% RH than pure trehalose, the higher volume of moisture and therefore the plasticizing effect of water did not promote the formation of trehalose dihydrate crystals. Note that the time at which the sample began to lose moisture, which is cited in the results of other researchers, could be inferred as the point of complete crystallization in samples. The moisture uptake after the visualized onset of crystallization would thus be associated with the portion of sample which has not crystallized. Sitaula et al. ("Moisture sorption characteristics and thermophysical properties of trehalose—PBS mixtures". Cryobiology. 2006. 52:369-385) asserted that adding PBS to trehalose lead to a shift from type II isotherm to type III. Based on the moisture content observed at both 11% and 61% RH, the addition of choline dihydrogen phosphate could also shift the isotherm from type II to type III, since type III isotherms generally have higher moisture contents at relatively high RH (61%) than their type II counterparts. Due to the plasticizing effect of water in trehalose glasses, higher moisture content in a given RH could decrease the $T_g$ of the mixture. If the glass transition temperature drops below the storage temperature, crystallization may occur in amorphous samples, which would have a detrimental effect on the preserved biomaterials. Based on the type of isotherm, the water sorption kinetics (adsorption or ab-sorption) can be resolved. For hydrophobic compounds, it is proposed that water molecule does not permeate through the sample volume and instead accumulates in area near to the surface of sample (i.e. adsorption).

Sodium Dihydrogen Phosphate

Figure 2:
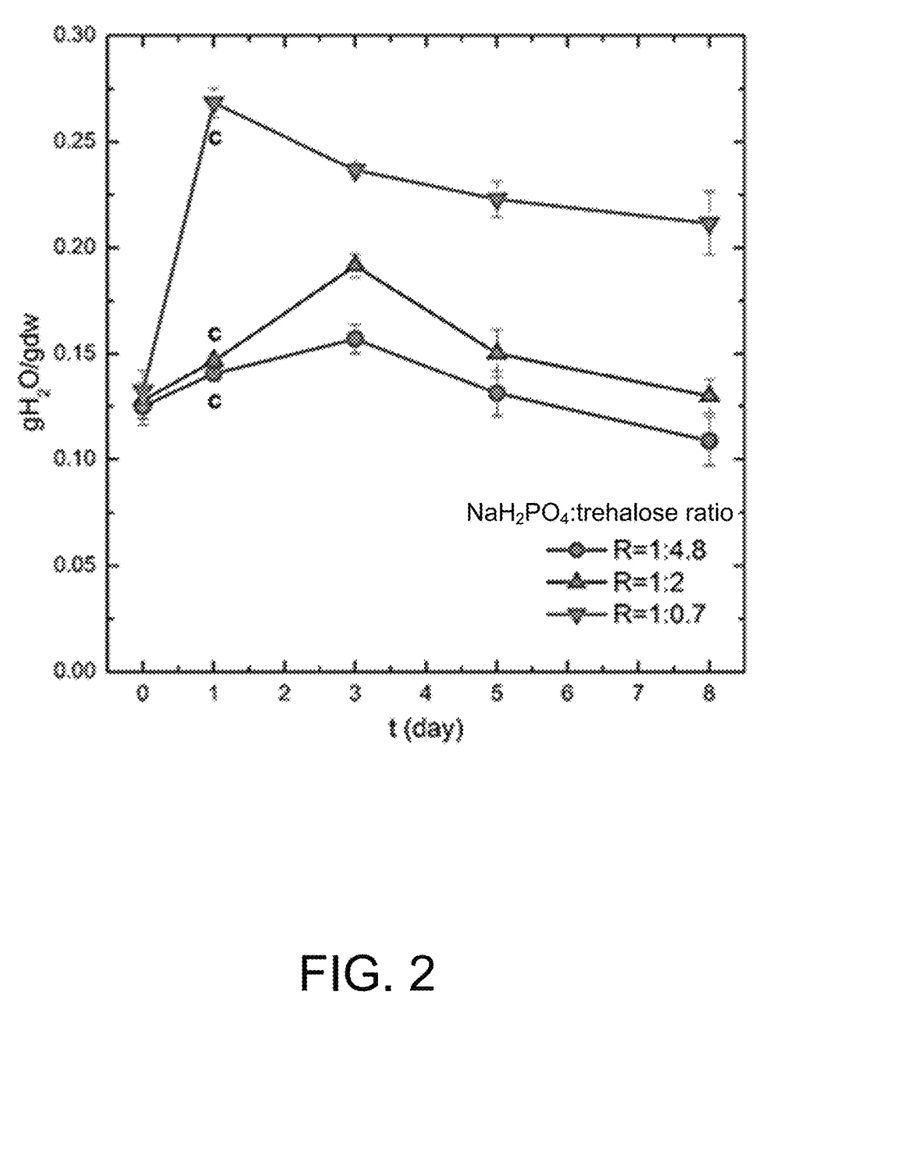
FIG. 2 is a graph illustrating moisture absorption kinetics in amorphous trehalose/$NaH_2PO_4$ with different ratios of $NaH_2PO_4$ to trehalose. The onset of crystallization as observed visually is indicated with the letter c.

The moisture absorption kinetics and the onset of trehalose crystallization in the amorphous trehalose/sodium dihydrogen phosphate systems were displayed in FIG. 2. It was found that the sugar crystallization occurred within 24 hours in all these samples. Samples with a higher molar ratio of $NaH_2PO_4$ to trehalose were found to absorb more moisture in the 61% RH environment. Similar to the profiles in FIG. 1, the moisture uptake profiles in FIG. 2 exhibited an initial increase in moisture content and then a decrease either directly after or about 2 days after the onset of the formation of trehalose dihydrate crystals.

For example, in the trehalose/sodium dihydrogen phosphate systems of R=1:0.7, crystallization was observed by day 1 and there was a major increase in the water content within the first 24 hours of storage in 61% RH (~0.27 $gH_2O/gdw$). Then the water content decreased continuously during the next 7 days after the onset of crystallization was observed. In the systems of lower molar ratios of $NaH_2PO_4$ to trehalose, the onset of crystallization was also observed at the same time period (day 1) but there was no evidence of a large pick in water sorption at day 1. In compositions with a 1:2 molar ratio the water content increased up to 0.18 $gH_2O/gdw$ after the visual onset of crystallization and decreased to 0.13 $gH_2O/gdw$ during the next 5 days. Moreover, samples with sodium as the cation held more moisture after the microwave processing at 11% RH, compared to equivalent compositions with choline as the cation (the end moisture content was all below 0.1 $gH_2O/gdw$ as seen in FIG. 1). On the whole, by substituting sodium for choline, all samples crystallized within 24 hours thus regardless of composition ratio, sodium dihydrogen phosphate as an additive did not delay crystallization.

Differences in the water content values between samples of different molar ratios of salt to trehalose equilibrated in 11% RH were not statistically significant. As the cation, sodium has a higher charge/size than choline, even though choline was found to be a better candidate cation for crystal suppression. This result is surprising in its contradiction with other results for inorganic salts. The superior performance of choline could be related to a different capacity of choline for interacting with other compositions or its capability for forming hydrogen bonds. Also, molecular weight can play a role in crystal suppression.

Sodium Hydrogen Phosphate

Figure 3:
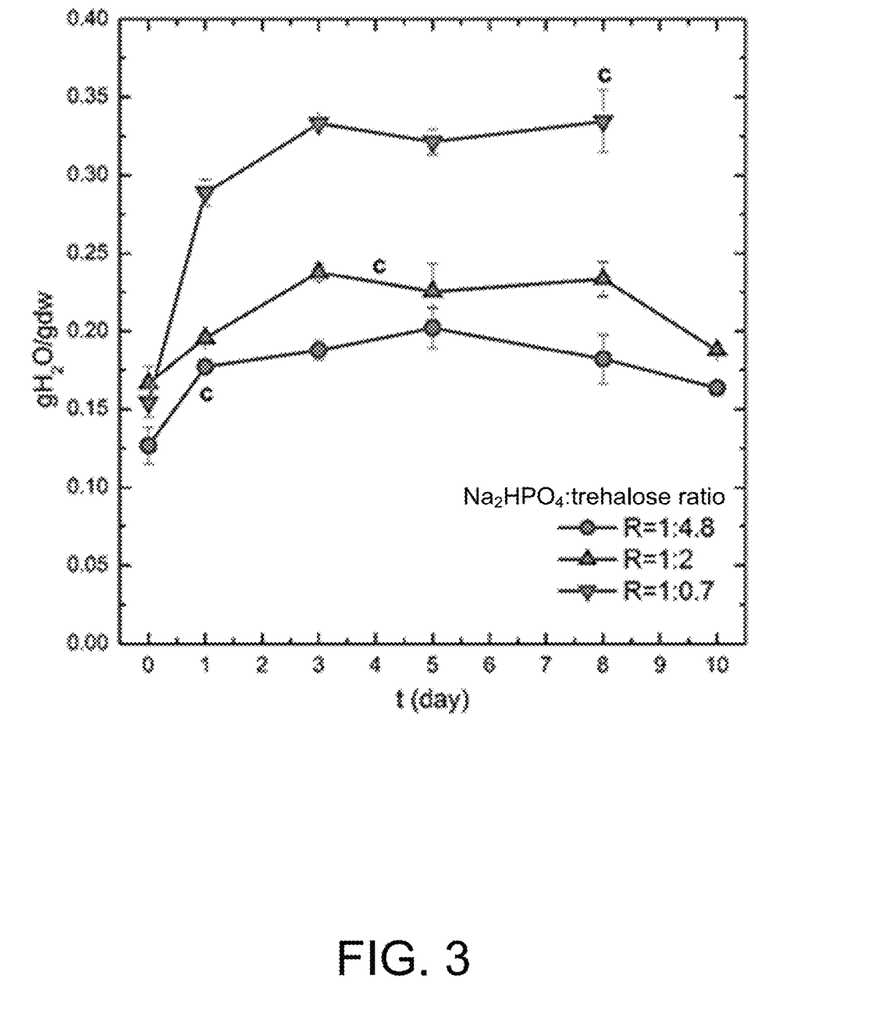
FIG. 3 is a graph illustrating moisture absorption kinetics in amorphous trehalose/$Na_2HPO_4$ with different ratios of $Na_2HPO_4$ to trehalose. The onset of crystallization as observed visually is indicated with the letter c.

FIG. 3 displays the water vapor absorption profiles for the trehalose/sodium hydrogen phosphate mixtures. It is evident that crystallization in the composition with the lowest molar ratio of $Na_2HPO_4$:trehalose occurred at a similar time interval as pure trehalose samples. But the increase in the molar ratio of $Na_2HPO_4$ to trehalose resulted in the increase in the crystallization suppression duration. It appears that the onset of crystallization is at least partially dependent on the molar ratio of $Na_2HPO_4$ to trehalose. For example, at a molar ratio of 1:4.8, the water content increased to 0.18 $gH_2O/gdw$ at day 5 with no significant moisture uptake at day 1 and then decreased over time. In this composition, crystallization was observed at day 1 with 0.17 $gH_2O/gdw$, which is higher than the water content of pure trehalose at the time of crystallization. In the case of the 1:2 molar ratio of $Na_2HPO_4$:trehalose, the water content increased until day 3 and after crystallization on day 4, the moisture content fluctuated and then started to decrease as a function of time. In the highest salt:sugar molar ratio, the water content almost doubled to 0.3 $gH_2O/gdw$ within the first 24 hours and then ascended gradually to 0.35 $gH_2O/gdw$ by day 3 and then fluctuated around this value before crystallization at day 8. Unlike the addition of sodium dihydrogen phosphate, the suppression of crystallization was directly correlated with the salt proportion in the mixture. In other words, the more $Na_2HPO_4$ there was in the mixture, the longer the delay before sugar crystallization. Moreover, the crystal suppression behavior as a function of salt ratio in the sodium hydrogen phosphate:trehalose mixtures is comparable to that of the choline dihydrogen phosphate:trehalose samples.

Choline Hydrogen Phosphate

The above results demonstrated that both the cation and anion could affect the suppression of trehalose crystallization. It was further realized that the combination of choline and hydrogen phosphate could potentially be an effective crystal inhibitor, because each of these ions was individually observed to have a crystal suppression effect. Therefore, the effects of choline as the cation together with hydrogen phosphate as the anion was tested and observed.

Figure 4:
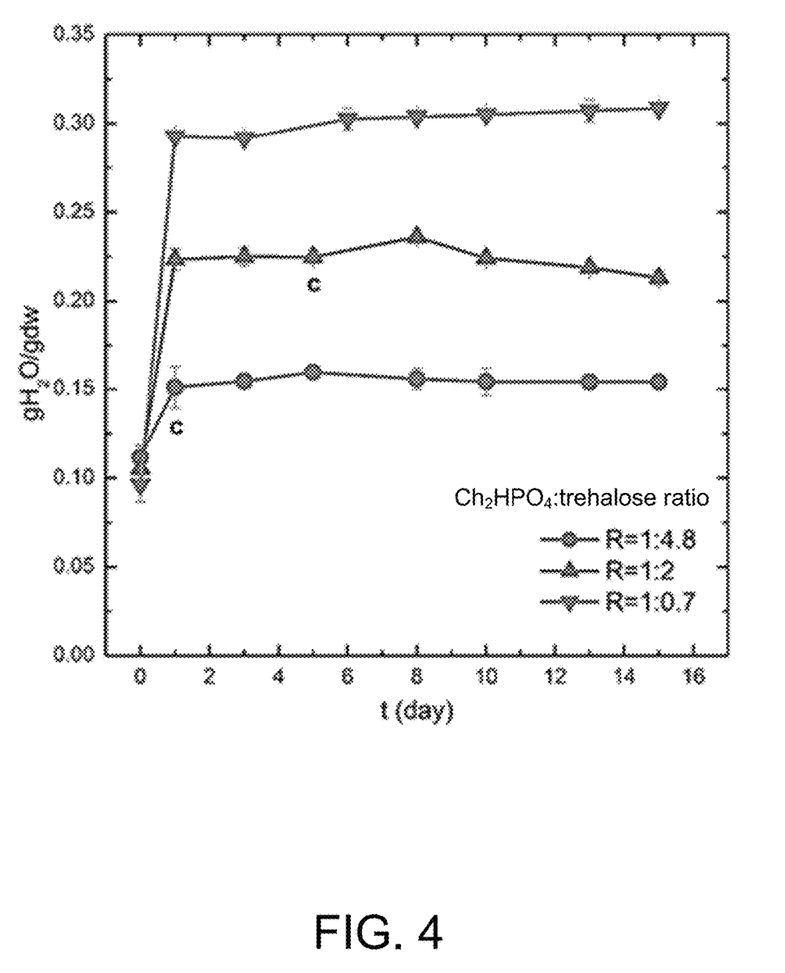
FIG. 4 is a graph illustrating moisture absorption kinetics in amorphous trehalose/$Ch_2HPO_4$ systems with different ratios of $Ch_2HPO_4$ to trehalose. The onset of crystallization as observed visually is indicated with the letter c.

At all molar ratios of choline hydrogen phosphate to trehalose, there was a distinct increase in the moisture uptake within 24 hours, and then the samples largely equilibrated at its highest water content. As observed previously, the samples with a higher salt to trehalose molar ratio absorbed more moisture. Results were similar to the previous results in this study about sodium hydrogen phosphate, with the exception of the 1:0.7 compositions in which no observed crystals formed within the observation period (15 days) even though all choline hydrogen phosphate:trehalose molar ratios were observed to have similar end moisture contents at 11% RH. Ohtake et al. ("Effect of pH, Counter ion, and phosphate concentration on the glass transition temperature of freeze-dried sugar-phosphate mixtures". Pharmaceutical Research 21, 2004. No. 9:1615-1621) found that phosphate ions in the form of hydrogen phosphate ($HPO_4^{2-}$) interacted with trehalose molecules. The results of the present example further demonstrated that, compared with sodium, choline is a better candidate cation for sugar crystal suppression. As discussed earlier, even though sodium has a higher charge/size in comparison with choline, the molecular weight appears to affect its role in crystal suppression. Furthermore, the crystal suppression property of choline could be related to the capacity of choline for interacting with other composition or its capability for making hydrogen bonds.

During the period of storage at 61% RH, the majority of moisture was absorbed into the samples within the first day. Within this span of time, the 1:0.7 ratio compositions had the largest increase in moisture absorption compared with the other two ratios. It was noticed that in the case of 1:0.7 ratio composition, the water content in the samples increased gradually after day one with no decrease, which is expected before the onset observation of crystallization.

Figure 5:
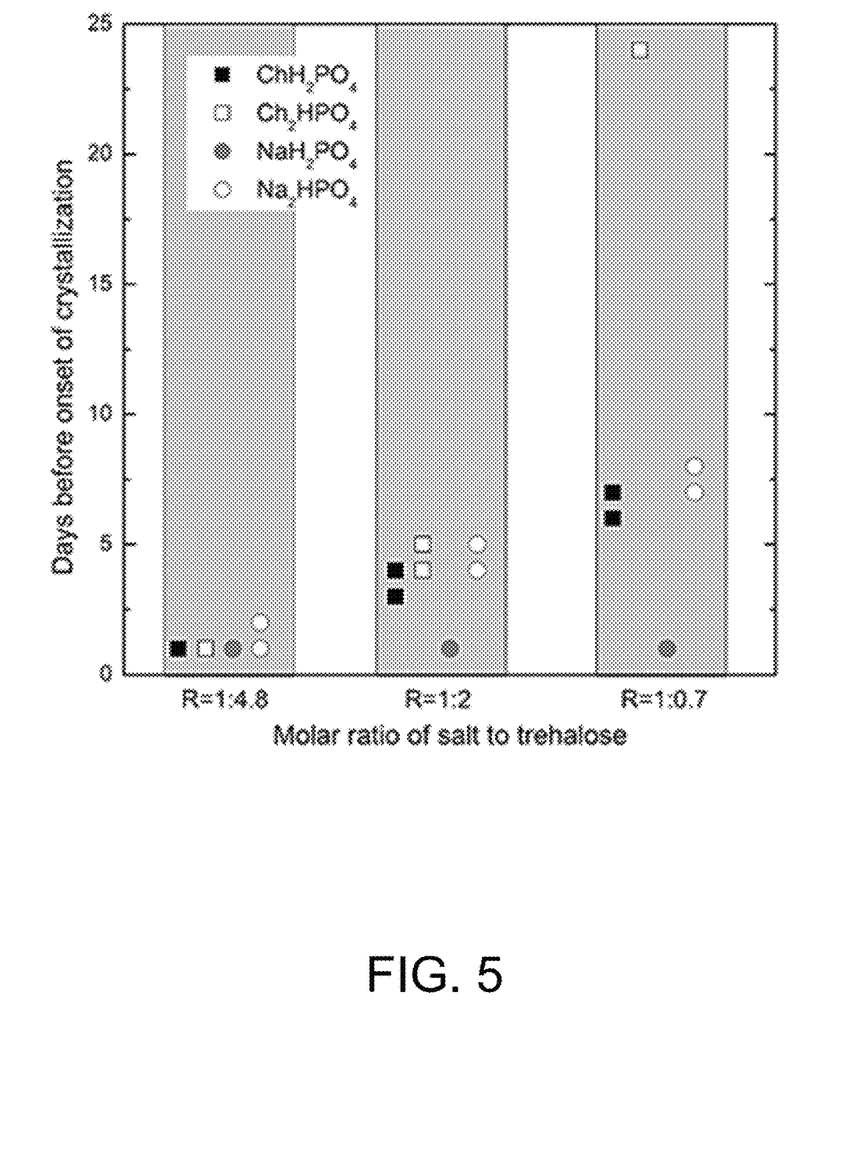
FIG. 5 is a graphic illustration of the time to crystallization (in days before onset of sugar crystallization) in the amorphous trehalose samples with ChH$_2$PO$_4$, NaH$_2$PO$_4$, Na$_2$HPO$_4$, and Ch$_2$HPO$_4$ (parallel replicates were monitored).

FIG. 5 shows the time (in days) before the onset of sugar crystallization in the different compositions studied. As seen in this figure, the replicates of each composition either crystallized on the same day or within 24 hours thereafter. Samples with a higher salt to trehalose molar ratio suppressed crystallization for a longer time, except for the sodium dihydrogen phosphate compositions. None of the trehalose/$Ch_2HPO_4$ samples (R=1:0.7) had crystallization within the period of observation (15 days), and after 24 days one of the samples exhibited what appeared to be tiny cracks.

CONCLUSIONS

The present example demonstrates that choline hydrogen phosphate ($Ch_2HPO_4$) is a promising agent for crystal suppression. In relatively high salt mass fraction of choline hydrogen phosphate the crystallization of trehalose was delayed for a considerable period of time (>2 weeks), and the samples absorbed a greater amount of water compared to pure trehalose. Depending on the mass fraction of salts, the water content increase ranged from 25% up to 145%. Increasing the water content can have a detrimental effect on the glass transition temperature and/or molecular mobility within the mixture, as water is a well-known plasticizer. However, in spite of this, the samples resisted crystal formation for much longer than pure trehalose samples or samples with the other choline and sodium salts.

Due to complexity of composition interactions in the mixture with three or more compounds, the glassy behavior of these mixtures can be complicated and difficult to predict, but it appears that the choline hydrogen phosphate composition suppresses potentially adverse crystallization effects. A high glass transition temperature is not the only influential parameter for choosing components as a protectant in the biopreservation applications. A good excipient acts through a combination of good glass forming abilities, effective interaction with biomolecules, and overall stability, and sometimes it is necessary to compromise between various desirable characteristics in order to achieve an effective composition for a given biomaterial. The use of choline hydrogen phosphate as an excipient in the food and biopreservation industries could help to reduce costs and other disadvantages of current storage and transport methods by suppressing crystallization at higher temperatures and greater humidity.

REFERENCES

Maria F. Mazzobre, Gonzalo Soto, José M. Aguilera, María P. Buera. 2000. "Crystallization kinetics of lactose in sytems co-lyofilized with Trehalose, analysis by differential scanning calorimetry". Food Research 34: 903-911.

Alexandra Simperler, Andreas Kornherr, Reenu Chopra, P. Arnaud Bonnet, William Jones, W. D. Samuel Motherwell, and Gerhard Zifferer. 2006. "Glass Transition Temperature of Glucose, Sucrose, and Trehalose: An Experimental and in Silico Study". Phys. Chem. 110: 19678-19684.

Danforth P. Miller, Rebeccah E. Anderson, Juan J. de Pablo. 1998. "Stabilization of lactate dehydrogenase following freeze-thawing and vacuum drying in the presence of trehalose and borate". Pharmaceutical Research 15, No. 8:1215-1221.

Lois M. Crowe, David S. Reid and John H. Crowe. 1996. "Is Trehalose Special for Preserving Dry Biomaterials". Biophysical 71: 2087-2093.

John H. Crowe, Lois M. Crowe, Ann E. Oliver, Nelly Tsvetkova, Willem Wolkers, Fern Tablin. 2001. "The Trehalose Myth Revisited: Introduction to a Symposium on Stabilization of Cells in the Dry State". Cryobiology 43: 89-105.

Amy M. Lammert, Shelly J. Schmidt, Gary A. Dayb. 1998. "Water activity and solubility of Trehalose". Food Chemistry 61: 139-144.

Ye Sun, Lei Zhu, Tian Wu, Ting Cai, Erica M. Gunn, Lian Yu. 2012. "Stability of Amorphous Pharmaceutical Solids: Crystal Growth Mechanisms and Effect of Polymer Additives". AAPS 14, No. 3: 380-388.

Alex Patist, Hans Zoerb. 2005. "Preservation mechanisms of Trehalose in food and biosystems". Colloids and Surfaces B: Biointerfaces 40: 107-113.

Nicole E. Hunter, Duncan Q. M. Craig, Peter S. Belton, Christopher S. Frampton. 2010. "The use of dynamic vapour sorption methods for the characterization of water uptake in amorphous trehalose". Carbohydrate Research 345: 1938-1944.

B. R. Bhandari, T. Howes. 1999. "Implication of glass transition for the drying and stability of dried". Food Engineering 40: 71-79.

Santanu Basu, U. S. Shivhare, and A. S. Mujumdar. 2006. "Models for Sorption Isotherms for Foods: A Review". Drying Technology 24: 917-930.

Brunauer, S., Emmett, P. H., Teller, E. 1938. "Adsorption of gases in multimolecular layers". American Chemists' Society 60: 309-319

G. K. van der Wela, O. C. G. Adan. 1999. "Moisture in organic coatings—a review". Organic Coatings 37: 1-14.

Shyam S. Sablani, M. Shatiur Rahman, Theodore P. Labuza. 2001. "Measurement of Water Activity Using Isopiestic Method". Protocols in Food Analytical Chemistry A2.3.1-A2.3.10.

Hector A. Iglesias, Jorge Chirife and Mar a P Buera. 1997. "Adsorption isotherm of amorphous trehalose". Sci Food Agric 75: 183-186.

Song Maio, Yrjo H. Roos. 2006. "Crystallization Kinetics and X-ray Diffraction of Crystals Formed in Amorphous Lactose". Food Science 70, No. 5:350-358.

M. F. Mazzobre, M. P. Longinotti, H. R. Corti, M. P. Buera. 2001. "Effect of Salts on the Properties of Aqueous Sugar Systems, in Relation to Biomaterial Stabilization". Cryobiology 43: 199-210.

Satoshi Ohtake, Carolina Schebor, Sean P. Palecek, Juan J. de Pablo. 2004. "Effect of pH, Counter ion, and phosphate concentration on the glass transition temperature of freeze-dried sugar-phosphate mixtures". Pharmaceutical Research 21, No. 9:1615-1621.

Ranjan Sitaula, Sankha Bhowmick. 2006. "Moisture sorption characteristics and thermophysical properties of trehalose—PBS mixtures". Cryobiology 52: 369-385.

D. P. Miller, J. J. de Pablo, H. R. Corti. 1997. "Thermophysical properties of trehalose and its concentrated aqueous solutions". Pharmaceutical Research 14, No. 7: 578-590.

Danforth P. Miller, Juan J. de Pablo, Horacio R. Corti. 1999. "Viscosity and Glass Transition Temperature of Aqueous Mixtures of Trehalose with Borax and Sodium Chloride". Phys. Chem. B 103: 10243-10249.

James J. Stachecki, Jacques Cohen and Steen Willadsen. 1998. "Detrimental Effects of Sodium during Mouse Oocyte Cryopreservation". Biology of Reproduction 59: 395-400.

Katherine D. Weaver, Regina M. Vrikkis, Matthew P. Van Vorst, Jonathan Trullinger, Ranganathan Vijayaraghavan, David M. Foureau, Iain H. McKillop, Douglas R. MacFarlane, Joanna K. Kruegerb and Gloria D. Elliott. 2012. "Structure and function of proteins in hydrated choline dihydrogen phosphate ionic liquid". Phys. Chem. 14: 790-801.

Lindong Weng, Ranganathan Vijayaraghavan, Douglas R. MacFarlane, Gloria D. Elliott. 2014. "Application of the Kwei equation to model the Tg behavior of binary blends of sugars and salts". Cryobiology 68: 155-158.

Lewis Greenspan. 1976. "Humidity Fixed Points of Binary Saturated Aqueous Solutions". Phys. Chem. 81A, No. 1:89-96

A. M. Elmonsef Omar, Yrjo H. Roos. 2007. "Glass transition and crystallization behaviour of freeze-dried lactose—salt mixtures". LWT—Food Science 40: 536-543.

Rahul Surana, Abira Pyne, Raj Suryanarayanan. 2004. "Effect of preparation method on physical properties of amorphous trehalose". Pharmaceutical Research 21, No. 7: 1167-1176.

D. J. Burnett, F. Thielmann, T. Sokoloski, J. Brum. 2006. "Investigating the moisture-induced crystallization kinetics of spray-dried lactose". Pharmaceutics 313: 23-28.

Carolina Schebor, María Florencia Mazzobrea, María del Pilar Bueraa. 2010. "Glass transition and time-dependent crystallization behavior of dehydration bioprotectant sugars". Carbohydrate Research 345: 303-308.

Richard W. Hartel, Roja Ergun, and Sarah Vogel. 2011. "Phase/State Transitions of ConfectionerySweeteners: Thermodynamic and Kinetic Aspects". Comprehensive Reviews in Food Science and Food Safety, Vol. 10: 17-32.

Iglesias, H. A., Chirife, J. 1976. "Prediction of effect of temperature on water sorption of food materials". Food Technology 11: 109-116.

Peleg, M. 1988. "An empirical model for the description of moisture sorption curves". Food Science 53: 1249-1251.

Robert B. Anderson. 1946. "Modifications of the Brunauer, Emmett and Teller Equation". American Chem. Society 68: 686-691.

Sun Y, Xi H, Chen S, Ediger M D, Yu L. 2008. "Crystallization near glass transition: transition from diffusion-controlled to diffusionless crystal growth studied with seven polymorphs". Phys. Chem. B 112: 5594-5601.

Tanaka H. 2003. "Possible resolution Kauzmann paradox in supercooled liquids". Phys. Rev. E 68: 1-8.

Martin Moskovits. 2005. "Surface-enhanced Raman spectroscopy: a brief Retrospective". Raman Spectroscopy 36: 485-496

M. Mathlouthi, B. Roge. 2003. "Water vapour sorption isotherms and the caking of food powders". Food Chemistry 82: 61-71.

The invention claimed is:

1. A method for preservation of a biomaterial comprising:
combining the biomaterial with a preservative composition comprising a sugar or sugar alcohol and a salt comprising choline hydrogen phosphate ($HPO_4^{-2}$) to form a mixture, wherein the salt in the preservative composition comprises 50% or more of $HPO_4^{-2}$ and 50% or less of choline dihydrogen phosphate ($H_2PO_4^-$); and
converting the preservative composition around, within, or around and within the biomaterial to an amorphous state.

2. The method of claim 1, wherein the sugar is selected from the group consisting of: sucrose, glucose, fructose, and trehalose.

3. The method of claim 1, wherein the sugar comprises trehalose.

4. The method of claim 1, wherein the biomaterial is selected from the group consisting of: living tissues, living cells, live viruses, polypeptides, nucleic acids, biomolecules, and combinations of these.

5. The method of claim 1, wherein converting the material to the amorphous state comprises processes selected from the group consisting of: cooling the material to a temperature less than the glass transition temperature of the composition, dehydration, or a combination of both cooling and dehydrating.

6. The method of claim 5, wherein the cooling or dehydration is selected from the group consisting of: freezing, freeze-drying, vitrification, cryopreservation, heat drying, microwave drying, lyophilization, use of a desiccant, airflow drying, spin drying, spray drying, and combinations thereof.

7. The method of claim 1, wherein the preservative composition forms an amorphous state matrix around, within, or around and within the biomaterial.

8. The method of claim 1, wherein the preservative composition suppresses crystal formation in the amorphous state preservative composition around, within, or around and within the biomaterial for a greater amount of time as compared to a biomaterial preserved with a comparative composition having the same formulation as the preservative composition except for having a greater amount of choline dihydrogen phosphate ($H_2PO_4^-$).

9. The method of claim 1, wherein the preservative composition has a salt:sugar ratio of about 0.1 to about 2.0.

10. The method for preservation of a biomaterial of claim 1, wherein the preservative composition has a pH of about 7.0 or greater.

11. A method of suppressing crystallization of a composition in an amorphous state comprising a sugar or sugar alcohol, the method comprising:
combining the sugar or sugar alcohol with a salt comprising choline hydrogen phosphate ($HPO_4^{-2}$) in an amount effective to increase the amount of time to formation of crystals in the composition when in the amorphous state as compared to a composition in the amorphous state made without the choline hydrogen phosphate or made with a greater amount of choline dihydrogen phosphate ($H_2PO_4^-$) than choline hydrogen phosphate.

12. A preservative composition comprising:
a sugar or sugar alcohol and
a salt comprising choline hydrogen phosphate ($HPO_4^{-2}$), wherein the choline hydrogen phosphate comprises 50% or more of the salt, the composition having a salt:sugar ratio effective to suppress the formation of crystals in the composition in the amorphous state such that the amount of time to formation of crystals in the presence of moisture is increased over the amount of time to crystal formation in a comparative composition that is the same as the preservative composition except for having a greater amount of choline dihydrogen phosphate ($H_2PO_4^-$) than the salt of the preservative composition.

13. The preservative composition of claim 12, wherein the salt:sugar ratio is from about 0.2 to about 2.0.

14. The preservative composition of claim 12, wherein the salt:sugar ratio is from about 0.5 to about 2.0.

15. The preservative composition of claim 12, wherein the salt:sugar ratio is between about 0.2 and 1.0.

16. The preservative composition of claim 12, wherein the composition has a pH of about 7.0 or greater.

17. The preservative composition of claim 12, wherein the composition has a pH between about 7.0 and 10.0.

18. The preservative composition of claim 12, wherein the sugar is selected from the group consisting of: sucrose, glucose, fructose, and trehalose.

19. The preservative composition of claim 12, wherein the sugar comprises trehalose.

20. The preservative composition of claim 12, wherein the salt comprises about 50% or less wt percent choline dihydrogen phosphate.

21. A composition comprising:
a living biomaterial, and
a preservative composition comprising a sugar or sugar alcohol and a salt comprising 50% or more of choline hydrogen phosphate ($HPO_4^{-2}$) and 50% or less of choline dihydrogen phosphate ($H_2PO_4^-$),
wherein the preservative composition is in an amorphous state and wherein the amount of time to formation of crystals in the presence of moisture is increased over the amount of time to crystal formation in a comparative composition comprising the biomaterial without the salt in the preservative composition comprising 50% or more of choline hydrogen phosphate.

22. The composition of claim 21, wherein the sugar is trehalose.

* * * * *